United States Patent [19]

Stern et al.

[11] Patent Number: 5,549,657
[45] Date of Patent: Aug. 27, 1996

[54] LOW PROFILE ADAPTOR FOR GASTROSTOMY FEEDING TUBE

[75] Inventors: David R. Stern, Grayson, Ga.; Michael Gauderer, Shaker Heights, Ohio; Albert N. Solbjor, Waltham, Mass.

[73] Assignee: C.R. Bard, Inc., Billerica, Mass.

[21] Appl. No.: 241,846

[22] Filed: May 12, 1994

[51] Int. Cl.⁶ ................................................ A61M 31/00
[52] U.S. Cl. .......................... 604/283; 604/250; 604/246
[58] Field of Search .................................... 604/104, 105, 604/167, 237, 247, 268, 270, 271, 283, 174, 246, 249, 250, 280, 256

[56] References Cited

U.S. PATENT DOCUMENTS

| | | | |
|---|---|---|---|
| 4,417,890 | 11/1983 | Dennehey | 604/256 |
| 4,424,833 | 1/1984 | Spector et al. | 137/849 |
| 4,473,369 | 9/1984 | Lueders | 604/244 |
| 4,557,261 | 12/1985 | Rügheimer | 128/202.27 |
| 4,774,944 | 10/1988 | Mischinski | 128/207 |
| 4,863,438 | 9/1989 | Gauderer | 604/247 |
| 4,944,732 | 7/1990 | Russo | 604/247 |
| 5,007,900 | 4/1991 | Picha et al. | 604/106 |
| 5,026,352 | 6/1991 | Anderson | 604/178 |
| 5,100,394 | 3/1992 | Dudar | 604/283 |
| 5,158,569 | 10/1992 | Strickland | 604/283 |
| 5,259,399 | 11/1993 | Brown | 128/897 |

OTHER PUBLICATIONS

*Gauderer™ Universal Gastrostomy Feeding Tube.*
*Ponsky™ "Pull" P.E.G. Tray with Soft Silicone Retention Dome—Instructions For Use;* Bard Interventional Products, C. R. Bard, Inc.; Reorder No. 000330.
*Bard® Guideware P.E.G. System with Soft Silicone Retention Dome—Instructions For Use;* Bard Interventional Products, C. R. Bard, Inc.; Reorder No. 000331.
*The Button;* Bard Interventional Products, C. R. Bard, Inc. Advertisement on P.R.G.™ Gastronomy Feeding Devices.
*Skin Level Permanent Feeding Gastrostromy;* Cohen, et al.; The American Journal of Surgery, vol. 141, Mar. 1981, pp. 391–392.
*Percutaneous Endoscopic Gastrostomy: Indications, Limitations, Techniques, and Results;* Ponsky et al.; World Journal of Surgery, vol. 13, No. 2, Mar./Apr. 1989, pp. 165–170.
*Feeding Gastrostomy Button: Experience and Recommendations;* Gauderer, et al.; Journal of Pediatric Surgery, vol. 23, No. 1 (Jan.), 1988, pp. 24–28.

Primary Examiner—Corrine M. McDermott
Attorney, Agent, or Firm—Darby & Darby, P.C.

[57] ABSTRACT

A low profile adaptor is disclosed for use with a gastrostomy feeding tube which has been inserted by means of conventional endoscopic procedures or with a replacement feeding tube inserted through the patient's stomach. The tube is cut to the approximate length by the surgeon. The adaptor comprises an anti-reflux valve assembly having a stem which can be plugged into the open end of the feeding tube. The valve assembly contains a seal which functions as a one-way valve to prevent reflux of gastric contents but which permits the introduction of feeding solution into the feeding tube. A clamp is placed around the feeding tube and the valve stem and locked into place to secure the valve assembly to the feeding tube at a location flush with the patient's skin. A silicone cover is placed around the clamp to protect the patient from skin irritation caused by the clamp, and also to protect the clamp and valve assembly from contamination.

13 Claims, 2 Drawing Sheets

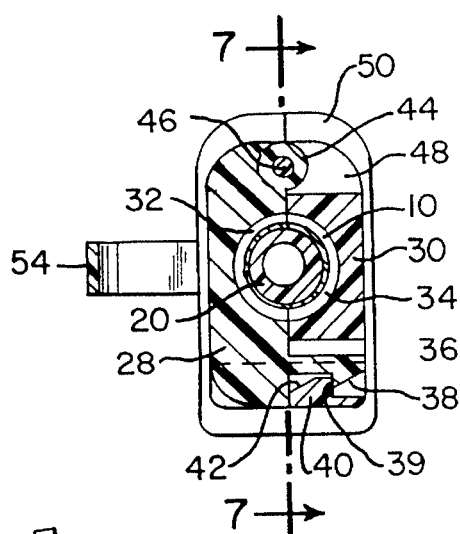
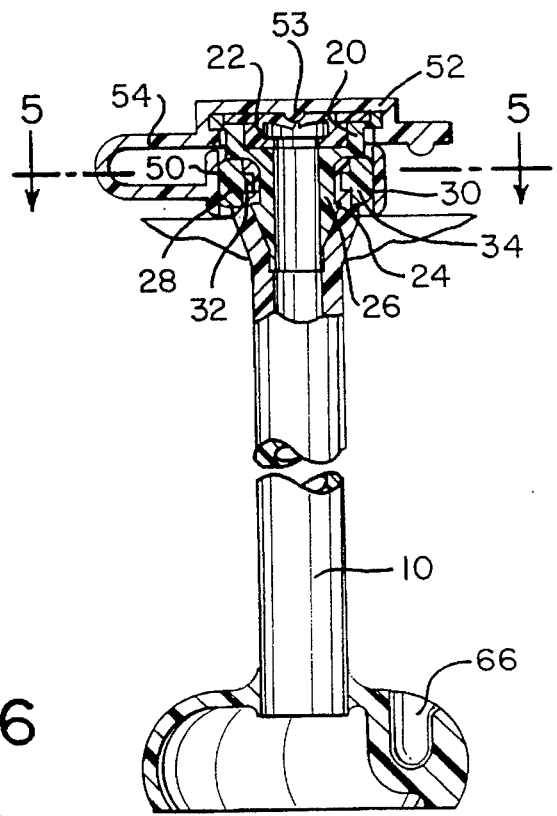
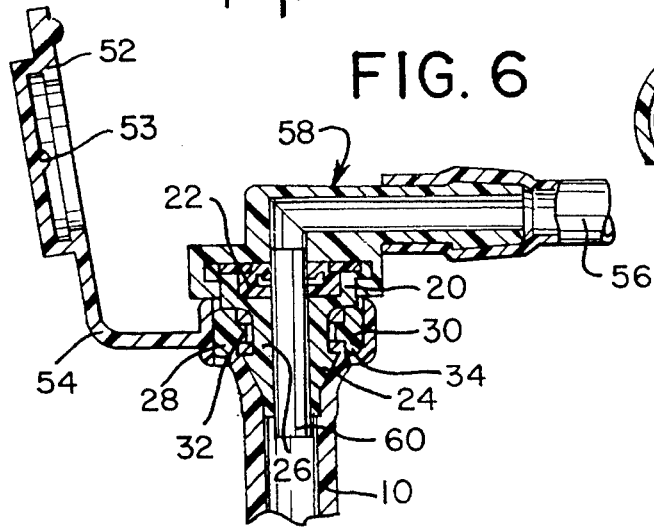
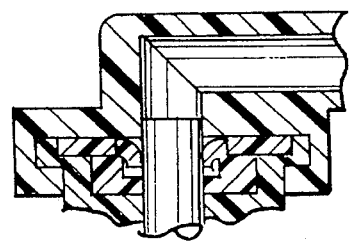
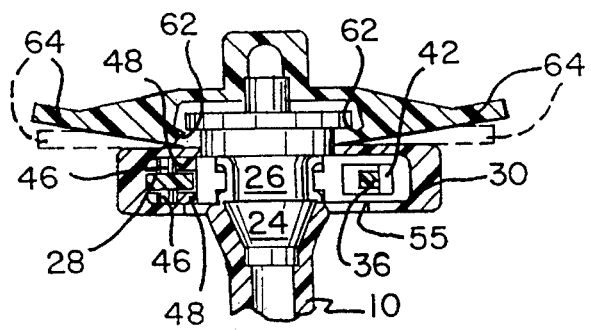

5,549,657

LOW PROFILE ADAPTOR FOR GASTROSTOMY FEEDING TUBE

This invention relates to an adaptor for use with a gastrostomy feeding tube.

BACKGROUND OF THE INVENTION

Gastrostomy is the creation of a temporary or permanent feeding tract between the stomach and the skin of the upper abdominal wall. It is used primarily to permit direct feeding for patients who cannot accept food orally. For example, gastrostomy is frequently required for patients unable to swallow as a result of central nervous system impairment resulting from any of a variety of causes.

Currently, gastrostomies are usually performed by endoscopic placement of a feeding tube in which a wire is passed into the stomach through the abdominal wall and the wire retrieved with an orally introduced endoscope. A feeding tube is secured to the wire and then pulled down the esophagus into the stomach and out through the abdominal wall. A retention dome on the distal end of the feeding tube retains the tube within the patient's stomach. This procedure is known as percutaneous endoscopic gastrostomy (PEG).

Intravenous or nasogastric feeding is typically indicated for short term feeding needs (e.g. post surgical patients), but percutaneous gastrostomy is the procedure of choice when long duration feeding requirements are anticipated. However, there are certain problems associated with long term use of a PEG feeding tube, the primary one being the inevitable deterioration of the tube over time. Even silicone feeding tubes eventually require removal and replacement. Moreover, the extension of the feeding tube externally of the gastrostomy site (stoma) may lead to inadvertent removal, leakage or adverse psychological consequences.

Because of these problems, various replacement feeding tubes have been proposed for introduction into an existing stoma site without the need to perform an additional endoscopic procedure. One such device is shown in Gauderer U.S. Pat. No. 4,863,438. This and other replacement devices have proven to be useful products in that (a) they are low profile, i.e. essentially flush with the skin thus avoiding problems associated with extended length feeding tubes, and (b) include one-way valves which prevent backflow of gastric contents (reflux). Nevertheless, despite the usefulness of such replacement products, it is necessary to first place a standard PEG tube and then remove the tube and insert the replacement device. Moreover, the length of the replacement device is likely to vary from patient to patient; therefore, hospitals must maintain an inventory of different sizes since the available replacement devices are not adjustable in size.

It would therefore be advantageous for both patient and physician to be able to convert a previously placed PEG feeding tube into a skin level feeding device having all the advantages of the currently available replacement devices and eliminating the need to remove the initially placed feeding tube and insert a replacement device.

A device which seeks to achieve the foregoing objective is disclosed in Cohen, O. M., et al.: Skin Level Permanent Feeding Gastrostomy, AM.J.Surg 141:391, 1981. This article discloses a feeding tube, inserted into the stomach through the abdominal wall, which is cut at skin level. A stainless steel hub is fitted tightly into the tube over a teflon plate, and a feeding adaptor screwed into the hub when the patient is to be fed. Between meals, the feeding adaptor is removed and the hub closed with a locking screw.

The object of this invention is to provide an improved device for adapting an endoscopically inserted gastrostomy tube for long term feeding procedures.

A more specific object of the invention is to provide an adaptor of the type described which is easier to insert and simpler to use during the feeding process than the Cohen et al. device.

A further object of the invention is to provide an improved adaptor for an endoscopically inserted gastrostomy tube which is also usable with a replacement device, thereby enabling the surgeon to adjust the length of a replacement device for individual patients.

SUMMARY OF THE INVENTION

The invention provides a low profile adaptor for use with a gastrostomy feeding tube which has been inserted by means of conventional endoscopic procedures or with a replacement feeding tube inserted through the patient's stomach. In either case, the tube is cut to the approximate length by the surgeon. The adaptor comprises an anti-reflux valve assembly having a stem which can be plugged into the open end of the feeding tube. The valve assembly contains a seal which functions as a one-way valve to prevent reflux of gastric contents but which permits the introduction of feeding solution into the feeding tube. A clamp is placed around the feeding tube and the valve stem and locked into place to secure the valve assembly to the feeding tube at a location flush with the patient's skin. A silicone cover is placed around the clamp to protect the patient from skin irritation caused by the clamp, and also to protect the clamp and valve assembly from contamination.

THE DRAWINGS

FIG. 4 is a side view partially in section of an adaptor in accordance with the invention;

FIG. 5 is a sectional view along the line 5—5 of FIG. 4.

FIG. 6 is a sectional view showing the feeding tube connected to an adaptor in accordance with the invention;

FIG. 6A is an enlarged sectional view showing the junction between the feeding connector and gasket; and FIG. 7 is a sectional view along the line 7—7 of FIG. 5.

DETAILED DESCRIPTION

Figure 1:
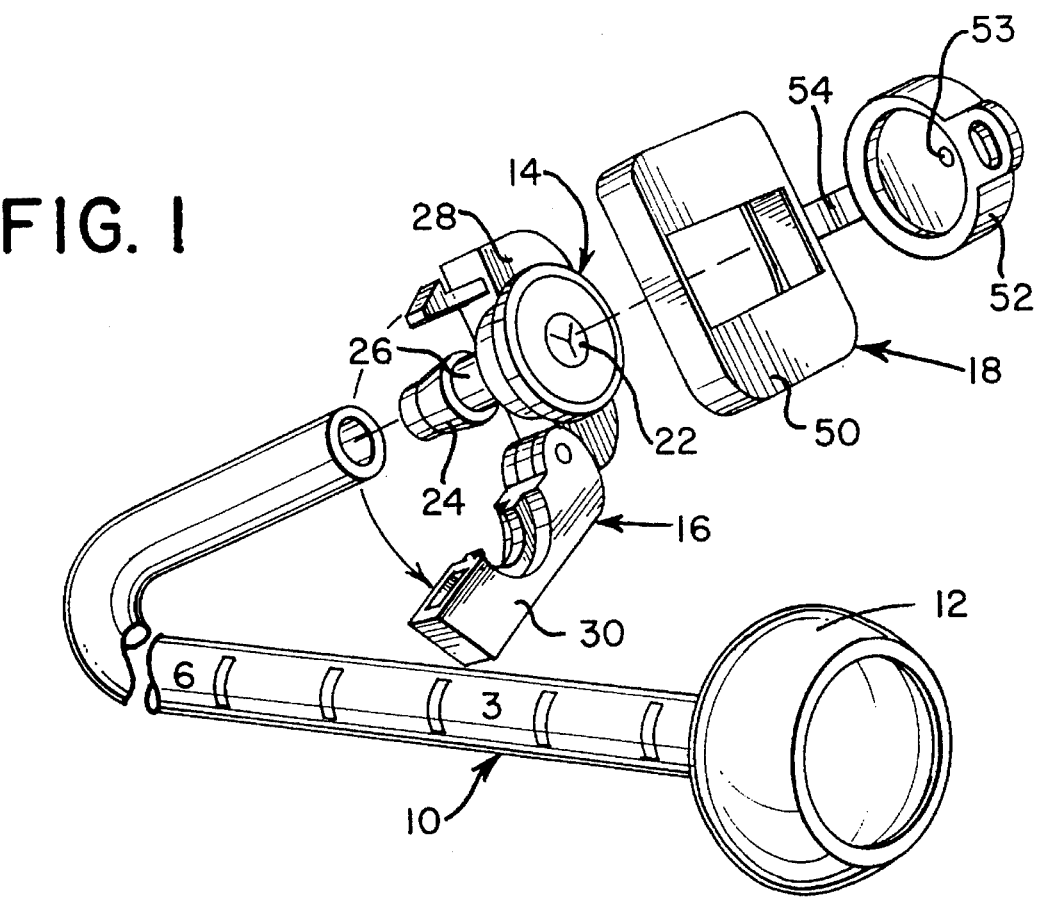
FIG. 1 is an exploded perspective view showing an adaptor in accordance with the invention attached to a standard gastrostomy feeding tube.
Figure 3:
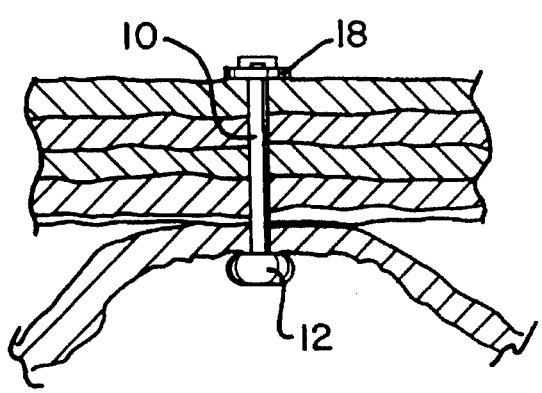
FIG. 3 is a schematic view showing how a feeding tube and adaptor in accordance with the invention is positioned within a patient.

FIG. 1 shows a gastrostomy feeding tube 10 terminating at its distal end in a retention dome 12. This may be a standard construction, which, as described above, is inserted in the patient as shown in FIG. 3 with the retention dome 12 within the patient's stomach and the feeding tube 10 extending through the patient's abdominal wall.

An adaptor in accordance with the invention comprises an anti-reflux valve assembly 14, a two-part clamp 16, and a silicone cover 18. As explained in further detail below, the valve assembly 14 includes a stem which is received in the proximal end of the feeding tube 10, and a gasket which prevents the discharge of material from the patient's stomach while permitting the introduction of feeding solution into the feeding tube 10. The clamp 16 retains the plug assembly within the feeding tube 10. The silicone cover 18 minimizes skin irritation, reduces contamination of the valve assembly 14 and provides a backup seal for the anti-reflux gasket within the valve assembly. The structural details of these components are illustrated in FIGS. 4–7 to which reference is now made.

Valve assembly 14 includes at its upper end a circular seat 20 in which a gasket 22 is positioned. The gasket may be made of silicone and have the cross-sectional shape shown in FIG. 6A with a Y-shaped slot in its exposed face (see FIG. 1) through which feeding solution can be introduced. A suitable gasket is shown and described in Spector et al. U.S. Pat. No. 4,424,833 which is hereby incorporated by reference into this specification. Gasket 22 prevents discharge of material from the stomach and is held in place by a ring 23 which is ultrasonically welded to the contiguous surface of valve seat 20. The construction and operation of the valve arrangement is conventional. The stem of valve assembly 14 includes a tapered and barbed distal (lower) end 24 and a waist portion 26. As shown in FIGS. 4, 6 and 7, the valve stem can be inserted into the proximal end of the feeding tube 10 to provide access to the feeding tube through the gasket 22.

Clamp 16 includes a male section 28 and a female section 30. The sections 28 and 30 include semicircular retention ribs 32 and 34, respectively, which are received within the waist portion 26 of valve assembly 12 to hold the valve assembly 14 within the proximal end of the feeding tube 10.

The male section 28 of the clamp includes a flexible prong 36 which terminates in a sloped follower surface 38 defining an undercut 39. The female section 30 includes an internal shoulder 40 having a sloped cam surface 42 which is engageable by the follower surface 30 when the clamp is closed (FIG. 5). The male and female clamp sections 28 and 30 are pivotally connected at the ends opposite prong 36 and shoulder 40 by means of oppositely extending pivot pins 46 (FIG. 7) extending from a mounting arm 44 of the male section 28 into suitable holes (not numbered) within bifurcated arms 48 of the female clamping section 30. When the clamp is closed, the undercut 39 engages the shoulder 40 as shown in FIG. 5 thereby locking the clamp closed to secure the adaptor to the feeding tube. Removal of the clamp is only possible by forcing prong 36 away from shoulder 40 so that the undercut 39 clears the shoulder.

Silicone cover 18 comprises a body portion 50 and a valve cap 52 connected by means of strip 54 to the body portion 50. Cap 52 includes an internal centering bead 53 which helps align the valve 22 and provides extra support for the valve when cap 52 is attached to the valve assembly. The body portion is molded to form pockets (not numbered) which receive the ends of the locked clamp sections 28 and 30 in a tight fitting relationship. An enlarged opening 55 is provided in the base of the silicone cap 18 to allow the cover to be applied and fit to clamp 16.

Figure 2:
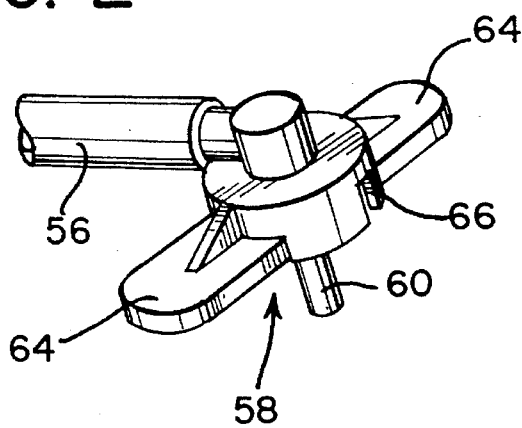
FIG. 2 is a perspective view showing the connector mechanism for attaching a conventional gastrostomy feeding tube to an adaptor according to the invention.

Numeral 56 (FIGS. 2 and 6) represents an external feeding tube through which feeding solution is to be provided to the patient. A connector 58 is attached to the distal end of the external feeding tube 56. The connector 58 connects the external feeding tube 56 to a hollow tube 60 which may be made of metal. The hollow tube 60 is inserted through the opening in ring 23 which helps guide the tube through the Y-shaped opening within gasket 22 to connect the external feeding tube 56 to the gastrostomy feeding tube 10 within the patient. Connector 58 includes opposed lips 62 (FIG. 7) which snap into the recess beneath circular seat 20 of the valve assembly 14 to secure the connector 58 to the valve assembly 14. The connector also includes opposed ears 64 and diametrically opposed slots 66 (one of which is shown in FIG. 2) which facilitate removal of the connector from the plug assembly. This is represented in FIG. 7 which shows the connector in dotted lines when it is snapped onto the valve assembly. The connector is shown in solid lines after an upward force has been applied to ears 64 to move the lips 62 out of the depression beneath the valve assembly seat 20.

In use, the gastrostomy feeding tube 10 is inserted by the physician as described above with the retention dome 12 properly seated within the stomach as represented in FIG. 3. The physician then cuts the tube 10 to the desired length and inserts the tapered barbed end of valve assembly 14 into the open end of tube 10. The clamp 16 is then placed around the tube 10 so that retention ribs 32 and 34 are adjacent to waist 34 of plug assembly 12. Pressure is applied to the free ends of the male and female sections 28 and 30 causing follower surface 30 of the flexible prong 28 to ride up and over cam surface 42 of shoulder 40 until it reaches the position shown in FIG. 5 where the prong snaps into its locking position against the shoulder 40. The silicone cover 18 is then placed over the clamp 16. The valve cap 52 may be snapped onto the valve assembly 12 as shown in FIG. 4 to protect the valve from external contaminants until the device is ready to be used.

When the patient is ready to be fed, valve cap 52 is removed and the connector 58 (which, of course, is attached to the feeding solution reservoir) plugged into valve assembly 12 as shown in FIGS. 6 and 7. This provides a conduit from the reservoir to the gastrostomy feeding tube 10. The connector is snap fit onto the valve assembly by means of the lips 62 as previously described. Despite the fact that the feeding connector is locked onto the valve assembly, relative rotation between the two is possible to allow for movement of the patient or the feeding solution reservoir. A benefit of the invention is that the connector 58 can also be used for gastric decompression; a separate decompression tube is not required.

The invention provides a number of advantages as compared to the prior art. The arrangement of the valve assembly, clamp and silicone cover enables the physician to form a fluid tight seal without an added surgical procedure. The valve assembly and clamp provide a secure, consistent assembly that will withstand not only daily feedings and use, but also the force required to remove the tube through the stoma tract, should this be desirable. Reflux is prevented by the self-sealing gasket within the valve assembly. During feeding, the gasket material forms a circumferential seal around the hollow tube 60. The silicone cover prevents skin irritation and also keeps the adaptor clean of gastric juices, feeding solutions and medications. The valve cap 52 provides backup support to the valve and helps reseat the valve after feedings because of the tight fit of bead 53 against the slitted sections of valve 22.

The invention has particular utility with replacement devices for gastrostomy feeding tubes. Existing replacement devices are sold in a limited number of discrete product lengths which are selected by the physician depending on the patient. It would be preferable to have a single length that could be cut to size by the physician at the time of insertion. The invention enables replacement devices to be provided in a single length and cut to size at the time of use. In the case of a replacement device, the retention dome 12 may include a pocket 66 adapted to receive a rigid obturator (not shown) which would permit the dome to be passed through an existing gastrostomy tract. The valve assembly 14, clamp 16 and silicone cover 18 could be attached to the feeding tube either before or after the replacement tube is introduced into the patient's stomach. This would enable the physician to size the tube specifically to each patient rather than having to rely on a limited number of discrete product lengths. As a replacement device, the invention provides improved flow of nutritional formula and allows for the introduction of jejunal feeding tubes prior to assembly of the valve, clamp and cover. Moreover, the spherical dome provides a superior seal against the inner-gastric wall (preventing leakage of gastric contents around the tube) and is easier to remove through the gastric-abdominal tract.

The clamp 16 should be easy to secure around the tube and valve assembly yet difficult to detach once assembled. The dimensions and geometry of the clamp should enhance the tensile strength between the relatively rigid clamp and valve assembly and the relatively elastic tubing. The material selected for the clamp must be strong enough and sufficiently rigid to provide for a stable and consistent clamping action yet it must be ductile enough to provide a snap fit assembly. In addition, the material must be highly stable, moisture and chemical resistant and biocompatible. Polyetherimide is suitable.

The hollow tube 60 may be made of plastic or metal (e.g. stainless steel); the silicone cover 18 of a biocompatible soft silicone to prevent skin irritation; and feeding connector 58 of low density polyethylene.

The valve assembly also may be made of polyetherimide. The tapered stem allows for easy insertion into the silicone tubing while the barb enhances the strength of the connection between the rigid and elastic components. The design may also permit the physician to observe the extent to which the silicone feeding tube extends above the clamp to ensure proper assembly of the components.

The fact that the valve is a self-sealing gasket within the valve assembly also is advantageous. First of all, it is not necessary to maintain the valve open to allow for gastric decompression. Also, the need for a secondary plug as required in certain existing replacement devices to seal the external portion of the feeding tube is eliminated. Moreover, a single connector 58 can be used to feed in or suction out of the stomach. Finally, if for some reason the valve is damaged or otherwise fails to seal properly, the valve assembly can be removed and replaced with a new assembly.

What is claimed is:

1. An adaptor combination for use with a gastrostomy feeding tube having a retention member at its distal end and an open proximal end, comprising:

an anti-reflux valve with an inlet and an outlet, said valve having a stem at its outlet constructed to be received into the feeding tube proximal end, said stem being tapered and including a waist portion, and a seal contained therein to event prevent reflux adapted to receive therethrough a supply tube to supply a feeding solution through said valve to the gastrostomy feeding tube;

a clamp constructed to clamp the gastrostomy feeding tube to said stem when said stem is received therein, said clamp being positioned over said waist portion when said stem is received in said gastrostomy feeding tube, to engage the gastrostomy feed tube against said stem waist portion; and a cover constructed to fit over and substantially cover said clamp.

2. The adaptor combination of claim 1, wherein said clamp includes male and female sections pivotally connected to each other at one end thereof and mating locking means at the opposite end of each said section for locking said male and female sections together to clamp said feeding tube to said anti-reflux valve stem.

3. The adaptor combination of claim 1, wherein said cover is of flexible material and includes a valve cap for covering said inlet and seal of said anti-reflux valve.

4. The adaptor combination of claim 1, further comprising a connector for supplying a feeding solution to said gastrostomy feeding tube, said connector including means for attaching onto said anti-reflux valve when engaged therewith and including a supply tube insertable through said seal to supply feeding solution to the gastrostomy feeding tube open proximal end when said means for attaching is engaged with said anti-reflux valve, said connector being rotatable relative to said valve.

5. The adaptor combination of claim 1 further comprising a gastrostomy feeding tube having a retention member in the form of a dome at its distal end with a portion for engaging tissue of a patient's body and an opening through which the feeding solution passes, the open proximal end of said gastrostomy feeding tube fitting over said valve stem to be clamped thereto by said clamp.

6. The adaptor combination of claim 1 wherein said valve and clamp are to be disposed on the exterior of the body of a patient's, and further comprising a gastrostomy feeding tube to extend through the patient body tissue, the open proximal end of said gastrostomy feeding tube connected to said valve stem by said clamp exterior of the body of the patient.

7. The adaptor combination of claim 6 further comprising a dome at the distal end of said gastrostomy feeding tube positioned to reside within the body of the patient to prevent said feeding tube from being pulled out, said dome having an opening through which the feeding solution is discharged into the patient's body.

8. The adaptor combination of claim 1 wherein said seal comprises a substantially flat gasket having a slit through which a feeding solution supply tube can pass.

9. In combination:

a gastrostomy feeding tube having a distal end, a retention dome at the distal end and an open proximal end;

an anti-reflux valve having an inlet and an outlet, said valve including a self-sealing gasket at its inlet which prevents reflux and is adapted to receive a supply tube to supply a feeding solution through said valve to the gastrostomy feeding tube proximal end, said valve including a stem received within said open proximal end of said feeding tube;

a clamp constructed to clamp said gastrostomy feeding tube to said stem when received in said tube and comprising male and female sections having first and second ends, and being pivotally attached to each other at said first ends thereof and including mating interlocking means at the second ends thereof for locking said clamping means to said feeding tube and said valve stem; and a cover of resilient material for substantially covering said clamp, said cover including a cap constructed to fit over and cover said reflux valve gasket.

10. The combination of claim 9 wherein said stem of said valve is tapered and includes barbed and waist portions, said clamp adapted to engage said stem waist portion.

11. The combination of claim 10, further comprising: a connector for supplying a feeding solution to said gastrostomy feeding tube, said connector including means to attach onto said anti-reflux valve and including a hollow tube insertable through said gasket, said connector being rotatable relative to said valve assembly.

12. The combination of claim 9, wherein said gasket is substantially flat and includes a Y-shaped slit, and said cap includes a centering bead adapted to contact said slit when covering said gasket.

13. The combination of claim 9, wherein a pocket is formed within the exterior surface of said dome and adapted to receive an obturator.

* * * * *